United States Patent
Feuer

(10) Patent No.: US 6,471,515 B2
(45) Date of Patent: Oct. 29, 2002

(54) DEVICE FOR HOLDING AN ABUTMENT

(76) Inventor: Marshall B. Feuer, 33000 Covington Club, #27, Farmington Hills, MI (US) 48330

( * ) Notice: Subject to any disclaimer, the term of this patent is extended or adjusted under 35 U.S.C. 154(b) by 0 days.

(21) Appl. No.: 09/759,063

(22) Filed: Jan. 12, 2001

(65) Prior Publication Data

US 2002/0094507 A1 Jul. 18, 2002

(51) Int. Cl.[7] ................................ A61C 3/00
(52) U.S. Cl. ...................... 433/162; 606/211
(58) Field of Search .................. 433/159, 160, 433/161, 162; 606/210, 211; 294/99.2, 33; 968/666, DIG. 1

(56) References Cited

U.S. PATENT DOCUMENTS

| | | |
|---|---|---|
| 90,319 A | 5/1869 | Somers |
| 482,232 A | 9/1892 | Delaney |
| 721,480 A | 2/1903 | Van Schott et al. |
| 772,324 A | 10/1904 | Asdell |
| 1,701,995 A | 2/1929 | Anderson |
| 2,595,683 A | 5/1952 | Lo Monte |
| 2,634,728 A | 4/1953 | Dale |
| 2,876,778 A | 3/1959 | Kees, Jr. ............... 128/346 |
| 3,291,476 A | 12/1966 | Calkin |
| 3,686,762 A | 8/1972 | Sutter ..................... 32/66 |
| 4,197,647 A | 4/1980 | Goldenthal ............ 433/159 |
| 4,487,580 A | 12/1984 | Ridgeway .............. 433/3 |
| 4,666,199 A | 5/1987 | Cheh ..................... 294/106 |
| 4,717,190 A | 1/1988 | Witherspoon ......... 294/99.2 |
| 5,007,827 A | 4/1991 | DiFranco .............. 433/4 |
| 5,120,221 A | * 6/1992 | Orenstein et al. ...... 433/159 |
| 5,261,813 A | 11/1993 | Baker .................... 433/3 |
| 5,339,712 A | * 8/1994 | Keyvani ................ 606/205 |
| 5,395,236 A | 3/1995 | Khouri .................. 433/4 |

FOREIGN PATENT DOCUMENTS

| | | |
|---|---|---|
| JP | 08215212 A | 8/1996 |
| JP | 09122147 A | 5/1997 |

OTHER PUBLICATIONS

Website printout of eTweezers.com products, Jan. 3, 2001.
Website printout of SPI Supplies products, Jan. 3, 2001.

* cited by examiner

Primary Examiner—Cary E. O'Connor
(74) Attorney, Agent, or Firm—Gifford, Krass, Groh, Sprinkle, Anderson & Citkowski, P.C.

(57) ABSTRACT

The current invention provides a device for holding dental abutments such as healing caps, healing screws, contoured healing abutments, PME (precision margin esthetics) abutments, PME impression pins, hexed transfer assemblies, straight and angled fixed system components, hexed coping screws or any dental implant parts when the object is being inserted or otherwise located into a patient's mouth. The device is tweezer-like and is designed to hold a dental abutment having a central axis. The device includes a pair of substantially identical members that are joined together at one of the ends and each have a free end. The members are disposed in the V-like configuration with the joined ends interconnected and the free end spaced apart so that when the members are squeezed towards one another, the free ends are brought into contact. Each of the members has a handle portion including the joined end, and an offset gripping portion. The gripping portion of each member has a junction segment which is joined to the handle portion and forms an interior angle in the range of 70–110 degrees with the handle portion. The gripping portion also has a grip segment with a first end joined to the junction segment and a second end configured to grip the dental abutment through cooperative action with the second end of the grip segment of the other member. When gripped, the dental abutment is retained at angle in the range of 60–90 degrees to the handle portion.

22 Claims, 4 Drawing Sheets

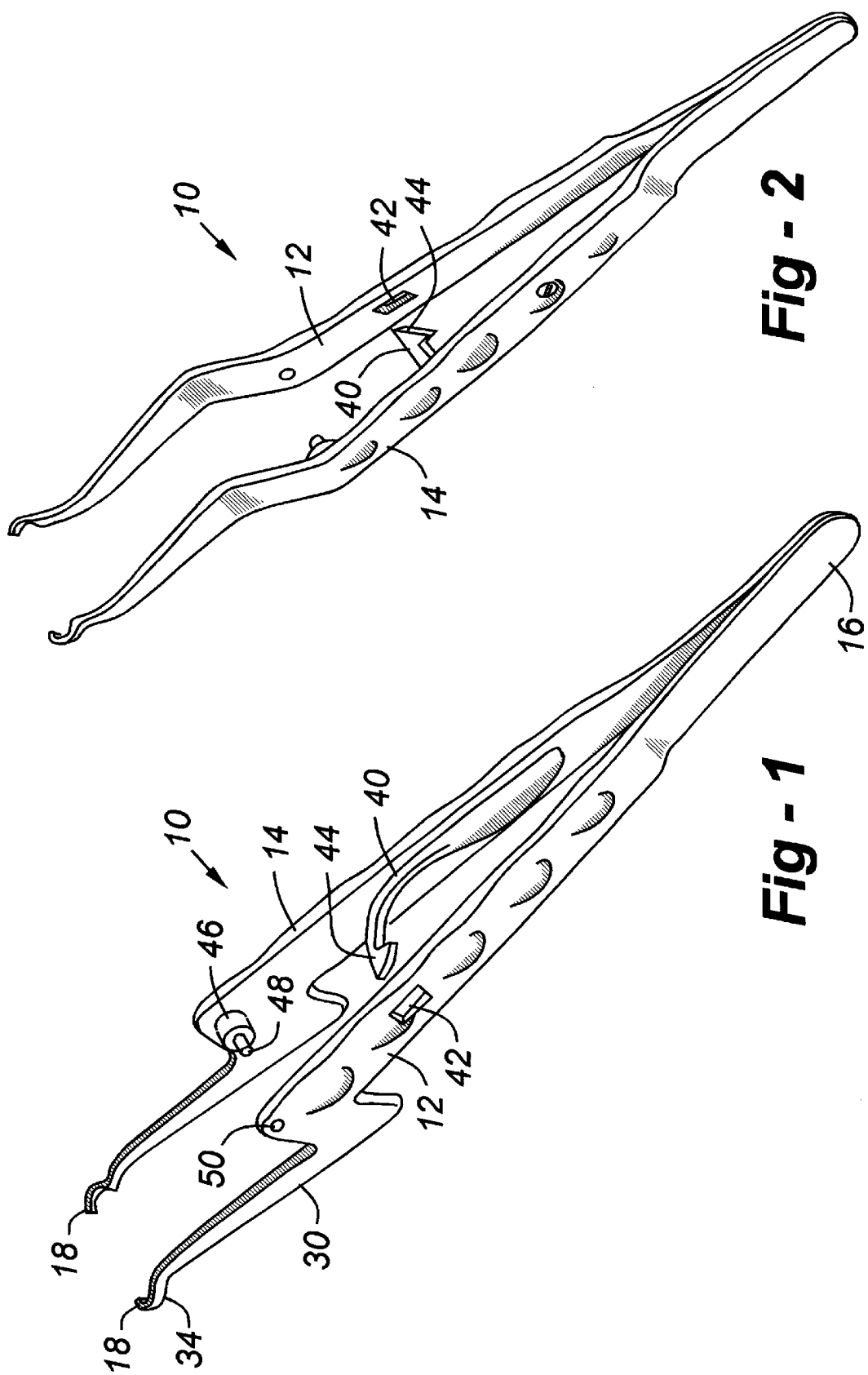

DEVICE FOR HOLDING AN ABUTMENT

FIELD OF THE INVENTION

The present invention relates to a device for holding an abutment during a dental procedure. The invention further relates to a device which can be used to hold healing caps, healing screws, contoured healing abutments, PME (precision margin esthetics) abutments, PME impression pins, hexed transfer assemblies, straight and angled fixed system components, and hexed coping screws.

BACKGROUND OF THE INVENTION

The handling of objects during a dental implant procedure has traditionally been a difficult task. The procedures involve the use of instruments and objects in a restricted area. The objects being inserted into the mouth are usually small, the environment in which they are placed is moist, and the teeth, tongue and cheeks all cause problems. The angle of approach when the objects are inserted into the mouth is difficult, especially when the objects are being positioned into the sides of the mouth. Additionally, the insertion of the objects is further complicated by the shape, material and size of the objects. Many of the materials used have slick surfaces, small flat surfaces or other surfaces which prevent stable gripping. The devices available to perform the function of gripping the various objects to be inserted into the mouth have typically been designed to address the problem of the small gripping area and problems associated therewith. These devices typically have scissor-like or tweezer-like designs which consist of two elongated pieces which are held together by some means. The operator grips the device at one end and the object to be inserted is held at the opposing end of the device.

One such design is shown in U.S. Pat. No. 4,197,647 ("the '647 patent"). This device is designed to hold crowns and has a curved insertion end with tips which are positioned in a manner which places the gripping surfaces at the front and the rear of the teeth. The device of the '647 patent is bulky and the grips will not accurately place an abutment for insertion. An additional problem with the '647 device is that it is usable on only half of the teeth. The operator must purchase two of the devices, the second being a mirror-image of the first device, to allow access to all teeth.

Other prior art devices such as U.S. Pat. No. 4,736,575 for holding dental floss, U.S. Pat. No. 5,290,171 a universal carrier, and U.S. Pat. No. 5,007,827 for orthodontic tweezers are available for inserting and gripping various objects within the mouth. However, none of the known devices address the issues of the awkward angle required when the object is being inserted into the rear of the mouth and the requirement of one instrument for use with all teeth.

SUMMARY OF THE INVENTION

The current invention provides a device for holding a dental object such as an abutment, healing cap, healing screw, contoured healing abutment, PME (precision margin esthetics) abutment, PME impression pin, hexed transfer assembly, straight and angled fixed system components, hexed coping screw or the like when the object is being inserted or otherwise located into a patient's mouth. The device according to the present invention is tweezer-like and has substantially identical first and second members each having a joined end and a free end. The members are disposed in an V-like configuration, with the joined ends interconnected and the free ends spaced apart such that as the members are urged towards one another, the free ends are urged into contact. Each of the members has a handle portion that includes the joined end, and an offset gripping portion. The gripping portion of each member has a junction segment which is joined to the handle portion and forms an interior angle in the range of 70–110 degrees with the handle portion. The gripping portion also has a grip segment with a first end joined to the junction segment and a second end configured to grip a dental abutment through cooperative action with the second end of the grip segment of the other member such that the central axis of the dental abutment is retained at an angle in the range of 60–90 degrees to the handle portion.

BRIEF DESCRIPTION OF THE DRAWINGS

A better understanding of the present invention will be had upon reference to the following detailed description when read in conjunction with the accompanying drawing in which:

FIG. 1 is a perspective view of a dental abutment holder according to the present invention;

FIG. 2 is a second perspective view of the device of FIG. 1 from a direction opposite to FIG. 1;

DETAILED DESCRIPTION OF THE INVENTION

Figure 3:
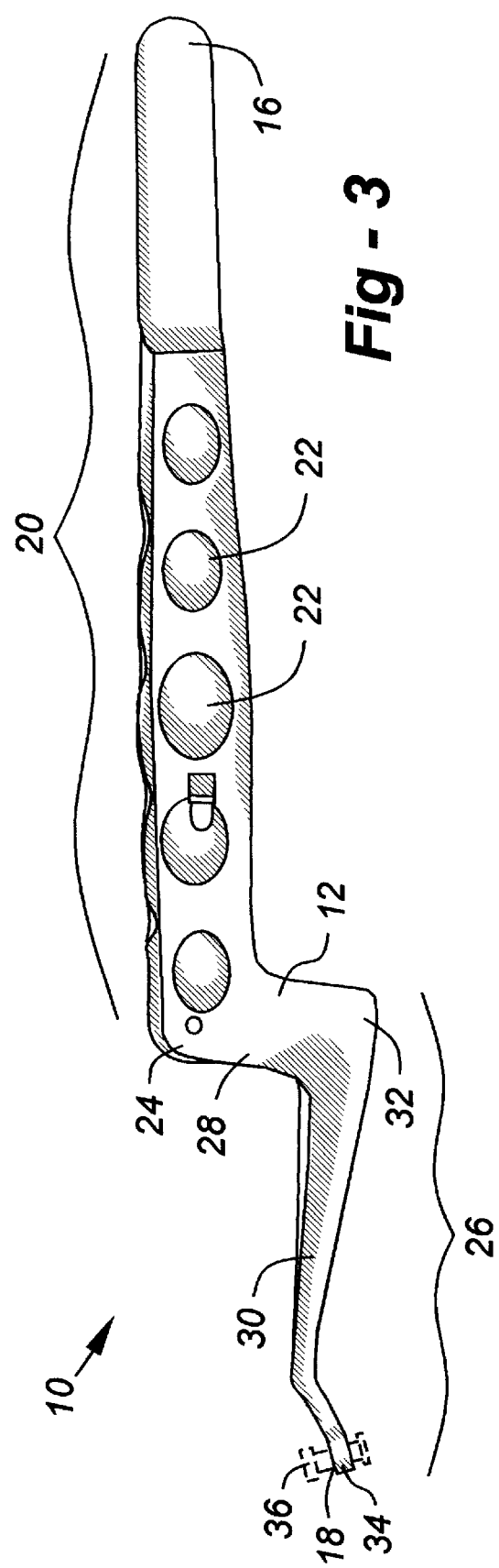
FIG. 3 is a side elevational view of the device of FIGS. 1 and 2.

Referring to FIGS. 1–3, a device for holding a dental abutment according to the present invention is generally shown at 10. As shown, the device is generally tweezer-like and includes a pair of arms or members 12 and 14 that are joined at one of their ends 16 and spaced apart at their other free ends 18, in a V-like arrangement. As with a pair of tweezers, squeezing the arms or members toward one another causes the free ends to come in contact. The device 10 may be held and used in a variety of orientations. Therefore, terms such as front, back, top, and bottom are arbitrary with respect to the actual device 10. However, for ease of description, portions of the device will be referred to herein as a front, back, top or bottom. For descriptional purposes only, FIG. 1 may be considered to be a top, front perspective view of the device 10 and FIG. 2 may be considered a bottom, back perspective view of the same device. Therefore, the portion of the device 10 which appears closest to the observer in FIG. 1 is the right end of the front side. FIG. 3 can then be defined as showing a front elevational view of the device 10 with the top of the device 10 closest to the top of the figure, the bottom of the device closest to the bottom of the figure, the right end of the device closest to the right edge of the figure and the left end of the device closest to the left edge of the figure. Referring again to FIG. 1, the device 10 has a front arm or member 12 and a back arm or member 14. Once again for definitional purposes, the front member 12 and back member 14 are considered to be substantially identical in that they have substantially the same height, width, shape, and silhouette when viewed from the front as shown in FIG. 3. The two members 12 and 14 do differ from one another in that certain portions are mirror images of each other and that the locking portion, and travel-limiting portion, to be described hereinbelow, are not symmetrical. However, for purposes of this application, the members are considered to be substantially identical.

Because the front arm or member 12 and back arm or member 14 are substantially identical, only the front arm or member 12 will be described in detail as to its configuration. The front member 12 includes a handle portion 20 which includes the joined ends 16. As shown, the handle portion 20 includes indentations 22 to assist in gripping the device 10. In the orientation shown in FIG. 3, the handle portion extends generally horizontally from the joined end 16 to what may be labeled as an opposite end 24. The member 12 also includes a gripping portion 26 which includes all of the member 12 other than the handle portion 20. As shown, the gripping portion is an offset gripping portion in that the majority of the gripping portion including the free end 18 is offset downwardly from the handle portion 20. The gripping portion 26 includes a junction segment 28 which is joined to the opposite end 24 of the handle portion 20 and extends downwardly therefrom. The gripping portion also includes a grip segment 30 with a first end 32, joined to the junction segment 28, and a second end 34. As shown, the gripping segment extends to the left from the lower end of the junction segment 28 in a direction similar to the handle portion. The second end 34 of the grip segment 30 forms a free end 18 of the entire front member 12. Referring again to FIG. 1, the second end 34 of the grip segment 30 is configured to grip a dental abutment through cooperative action with the second end of the grip segment of the back member 14. As shown, the second end of each of the grip members is configured so as to grip a cylindrical-shaped object. As will be clear to those of skill in the art, some dental abutments used in dental procedures have a portion which is generally cylindrical or conical. The second ends of the grip segments of the members 12 and 14 are shaped so as to cooperate to grip this cylindrical or conical portion. Preferably, each second end is half of a circular surround such that when the two second ends are joined, a cylindrical hole is formed. FIG. 3 shows, in dotted lines, an abutment 36 being gripped by the second ends of the grip segments of the two members 12 and 14.

As will be clear to those of skill in the art, the illustrated shape of the device 10 according to the present invention provides numerous advantages over the prior art. The offset gripping portion 26 essentially forms a step in the device 10 between the joined ends 16 and free ends 18 of the member 12 and 14. This step or offset significantly improves the operator's ability to view the free ends 18 of the device, an abutment being gripped therein, and various portions of the patient's mouth as work is being done. The shaft of the device 10 also allows it to be used to access all parts of the patient's mouth. For example, if the operator grips the device 10 from above in the position shown in FIG. 1, they may easily access the rear of the patient's jaw. By rotating the device to the position shown in FIG. 2, other portions of the mouth may be accessed.

Referring again to FIGS. 1 and 2, it can be seen that the device 10 may be operated by squeezing the handle portions of the members 12 and 14 towards one another so as to bring the free ends 18 of the members 12 and 14 together to grip an abutment. In the illustrated embodiment of the present invention, a locking device is provided to retain the front and back members 12 and 14 in a locked position. That is, the locking device retains the members 12 and 14 in a position wherein the free ends 18 are merged into contact. As will be clear to those of skill in the art, locking of the arms 12 and 14 may be achieved in various ways. In the illustrated and preferred embodiment, a resilient locking arm 40 extends from the inside of the back member 14 towards the inside of the front member 12. A passage 42 is defined through the front member 12 and is aligned with the end of the locking arm 40. The end of the locking arm includes a detent 44 that interlocks with the passage 42 once the tip of the arm 40 passes therethrough. In operation, the operator squeezes the arms 12 and 14 towards one another causing the tip of the locking arm 40 to extend through the passage 42. Because of the position of the arm 40, this causes the arm 40 to bend slightly to allow the detent 44 to pass over one edge of the passage 42. Once the detent 44 passes entirely through the passage 42, it clicks into place causing the members 12 and 14 to be locked into this configuration. To unlock the device, the operator presses against the end of the locking arm 40 to slightly bend the arm such that the detent 44 can clear the edge of the passage 42, allowing the device 10 to unlock. A travel limit is also provided. The travel limit consists of a cylindrical protrusion 46 extending from the inside of the back member 14 towards the inside of the front member 12. The cylindrical protrusion is positioned on the inside of the handle portion on the area previously designated as the opposite end 24. The cylindrical protrusion 46 is sized so as to prevent the front member 12 and back member 14 from coming into too close of contact and thereby bending or overstressing the device 10. An alignment pin 48 extends from the center of the cylindrical protrusion 46 and aligns with an alignment hole 50 in the opposite end 24 of the handle portion 20 of the front member 12. When the front and rear members 12 and 14 are urged together, the pin 48 enters the alignment hole 50 prior to the cylindrical protrusion 46 touching the inside of the front member 12.

As will be clear to those of skill in the art, the exact dimensions and angles as illustrated in the body of the present invention may be altered without departing from the scope and teaching of the present invention. However, for purposes of clarity, the dimensions and angles of the illustrated embodiment of the present invention will be discussed in more detail with reference to FIGS. 4 and 5.

Figure 4:
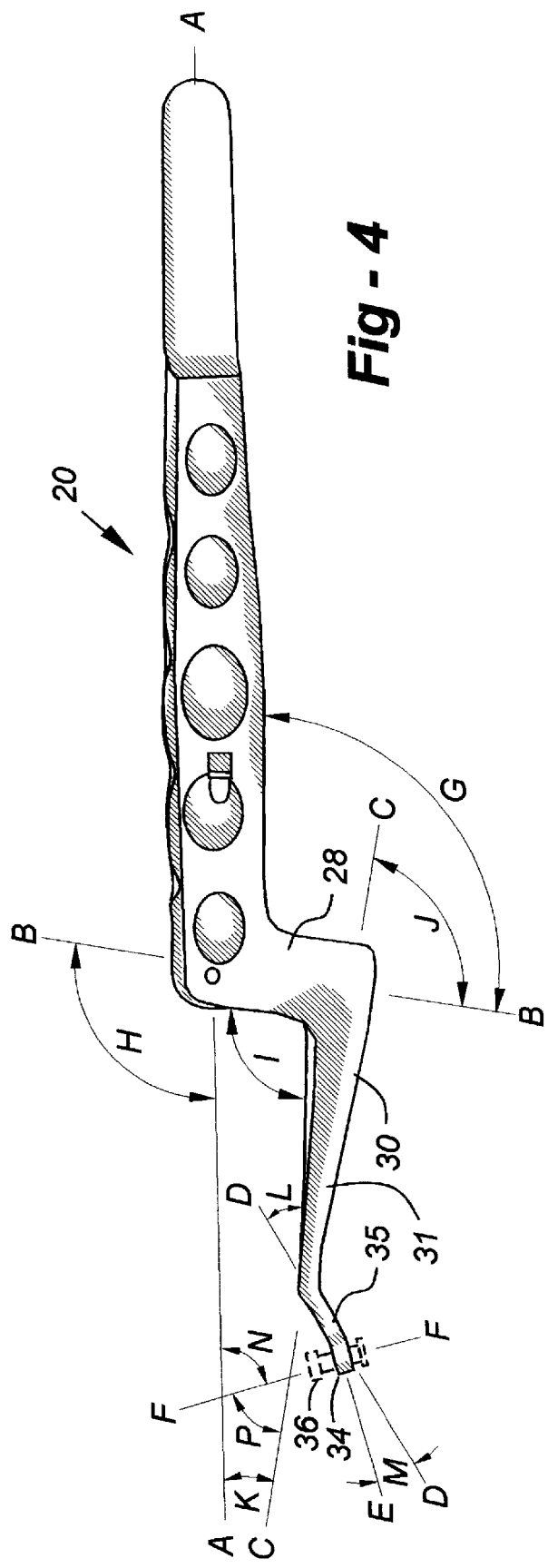
FIG. 4 is a side elevational view similar to FIG. 3 showing the angles between various portions of the device.

As shown in FIG. 4, the handle portion 20 is generally straight and may be said to extend on along a first direction. The central axis of the handle portion is generally indicated by line A—A and the first direction may be considered to align with line A—A. The junction segment 28 extends in a second direction generally defined by the central axis of the junction segment shown by line B—B. The grip segment 30 extends in a third direction generally defined by the central axis of the grip segment and indicated by line C—C. As shown, the grip segment, in the illustrated embodiment, actually has multiple bends. Specifically, the majority of the grip segment 30 extends along line C—C. This will be called the main portion 31. The extreme end of the grip segment 30 was previously labeled as the second end 34. A short mid-portion 35 interconnects the main portion 31 of the grip segment 30 with the second end 34. This mid-portion 35 extends in a fourth direction at an angle to the main portion 31 of the grip segment 30. This fourth direction is generally indicated by lines D—D. As shown, this mid-portion 35 bends slightly downwardly from the main portion 31 of the grip segment 30. The second end 34 then bends slightly back upwardly from the mid-portion 35. The central axis of the second end 34 is generally indicated by line E—E. An abutment 36 is shown retained in the second end 34. As will be clear to those of skill in the art, such an abutment may be considered to have a central axis, which is indicated in FIG. 4 as line F—F. For abutments which are not symmetrical or otherwise do not have an easily defined central axis, the central axis is defined, for purposes of this disclosure, as being through the center of the opening formed by the second ends, and perpendicular to the line E—E and to a plane containing the perimeter of the opening. The axis of the abutment may also be defined as the central axis of the cylindrical opening defined by the second ends.

In this preferred embodiment, the angle between the handle portion 20 and the junction segment 28 is the angle between the line A—A and the line B—B. The inside angle between these two is indicated by angle G. This angle is also shown by angle H. Preferably, the inside angle between the junction segment 28 and the handle 20 is in the range of 70–110 degrees. More preferably, the angle is between 85 and 100 degrees. In the illustrated embodiment, the angle measures approximately 96 or 97 degrees. These angles, and ranges of angles, are also the angles between the first direction and the second direction, as previously defined. The inside angle between the grip segment 30 and the junction segment 28 is indicated by angle I and may be also measured as angle J. The angles I and J are preferably in the range of 70–110 degrees. Even more preferably, they are in the range of 85–95 degrees. In the illustrated embodiment, the angles are approximately 88 degrees. The angle between the grip segment 30 and the handle portion 20 is indicated by angle K and, in the illustrated embodiment, is approximately 90 degrees. As mentioned previously, the mid-portion 35 of the grip segment 30 is angled to the main portion 31 of the grip segment 30. The angle between the mid-portion 35 and the main portion 31 of the grip segment 30 is indicated by angle L between line D—D and line C—C. This angle may be in the range of 0–60 degrees, and more preferably in the range of 30–50 degrees. In the illustrated embodiment, the angle is approximately 44 degrees as measured between the central axis of the majority of the grip portion 30 and the mid-portion 35. Because the majority of the grip segment 30 is tapered, the angles will be different if measured from the upper or lower surface.

As mentioned previously, the second end 34 is angled to the mid-portion 35, as indicated by angle M between line E—E and D—D. This angle may be in the range of approximately 0–30 degrees, and in the illustrated embodiment is approximately 21 degrees. An abutment retained in the second end 34 is held at an angle to the handle portion 20, as indicated by the angle between lines F—F and line A—A and indicated by angle N. This angle may be in the range of 60–90 degrees, and more preferably in the range of 70–80 degrees. In the illustrated embodiment, the angle is approximately 76 degrees. The angle between the central axis of the abutment 36 and the grip segment 30 is shown as angle P. Angle P, in the illustrated embodiment, is approximately 23 degrees.

Figure 5:
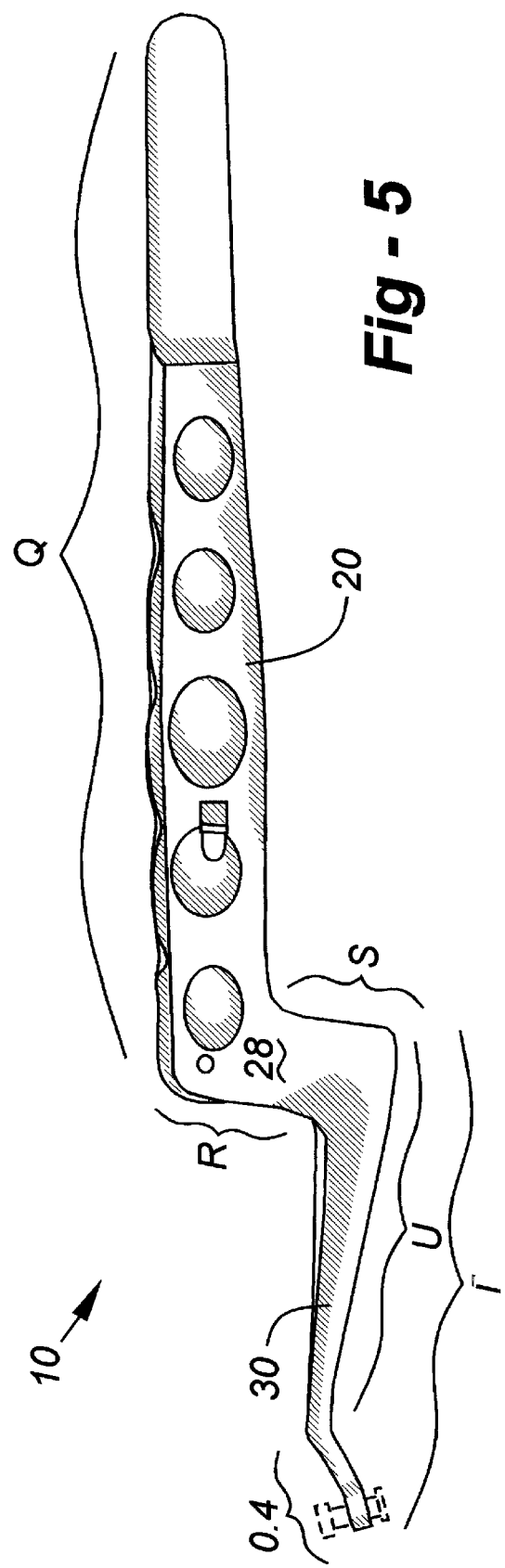
FIG. 5 is a side elevational view similar to FIGS. 3 and 4 showing dimensions of various portions of the device.

Referring now to FIG. 5, the dimensions of the device 10 will be described. The length of the handle 20 is generally indicated by Q and is approximately 4.25 inches. The length of the junction segment 28 is generally indicated by R and S and is approximately 0.5 inch. This is also the distance between the center lines of the grip segment 30 and the handle portion 20 or the distance between line A—A and line C—C in FIG. 4. The total length of the grip segment 30 is indicated by T and is approximately 2.0 inches. As previously mentioned, the majority of the grip segment 30 extends in one direction and its majority portion has a length indicated by U of 1.6 inches. The length of the mid-portion and the second end of the grip segment 30 is approximately 0.4 inch. The device 10 is designed to grip dental abutments. These abutments come in a wide variety of sizes and shapes and the device is designed to grip all of them. For this purpose, the cylindrical opening in the second ends of the grip segments, when they are adjacent one another and forming a cylindrical opening, is between 3 and 3.5 mm. Obviously, this opening may be larger or smaller without departing from the scope of the invention. The dimensions illustrated in FIG. 5 may also be altered without departing from the scope of invention.

The device 10 is preferably constructed of a material such as stainless steel. Such material is capable of accepting permanent welds at the joined ends and is also flexible enough to allow the free ends to be brought into contact with fingertip pressure. Stainless steel also has a sanitary appearance and tolerates cleaning and sterilization.

As will be known to those of skill in the art, other variations may be made on the disclosed versions of the present invention without departing from the scope or teaching of the present invention. It is the following claims, including all equivalents, which define the scope of the present invention.

I claim:

1. A tweezer-like device for holding a dental abutment having a central axis, the device comprising:
    a substantially identical first and second member each having a joined end and a free end, the members being disposed in a V-like configuration with the joined ends interconnected and the free ends spaced apart such that when the members are urged towards one another, the free ends are urged into contact;
    each of the members further having a handle portion including the joined end, and an offset gripping portion;
    the gripping portion of each member having a junction segment joined to the handle portion and forming an interior angle in the range of 70 to 110 degrees with the handle portion, the gripping portion further having a grip segment having a first end joined to the junction segment and a second end configured to grip the dental abutment through cooperative action with the second end of the grip segment of the other member such that the central axis of the dental abutment is retained at an angle in the range of 60 to 90 degrees to the handle portion; and
    a locking device operable to selectively retain the first and second members in a position such that the free ends are in contact, the locking device comprising a locking arm extending from the first member and selectively engaging the second member.

2. The device according to claim 1, wherein the grip segment forms an interior angle in the range of 70 to 110 degrees with the junction segment.

3. The device according to claim 2, wherein the angle between the grip segment and the junction segment is in the range of 85 to 95 degrees.

4. The device according to claim 1, wherein the grip segment includes a main portion including the first end and a mid-portion between the main portion and the second end, the mid-portion being angled with respect to the main portion.

5. The device according to claim 4, wherein the angle between the mid-portion and the main portion is in the range of 30 to 50 degrees.

6. The device according to claim 4, wherein the second end is angled with respect to the mid-portion, the angle being in the range of 0 to 30 degrees.

7. The device according to claim 1, wherein the angle between the mid-portion and the main portion is in the range of 0 to 60 degrees.

8. The device according to claim 1, wherein the second end of each of the grip segments comprise an arcuate member such that when the two second ends are brought into contact, a generally round hole is formed therebetween.

9. The device according to claim 8, wherein the hole had a diameter between 3 and 4 millimeters.

10. The device according to claim 1, wherein the first end of the grip segment is offset from the central axis of the handle portion by a distance of at least 0.3 inches.

11. The device according to claim 10, wherein the distance is approximately 0.5 inches.

12. The device according to claim 1, wherein the angle between the handle portion and the junction segment is between 96 and 97 degrees.

13. The device according to claim 1, wherein the dental abutment is retained at an angle of approximately 76 degrees.

14. The tweezer-like device according to claim 1, wherein the second member has an opening defined therein and the locking arm has a connected end that is connected to the first member and a locking end with a detent defined thereon, the locking arm configured such that the locking end passes through the opening when the members are urged toward one another and the detent engages the opening in the second member to retain the free ends of the members in contact.

15. The tweezer-like device according to claim 14, further comprising a travel limiter disposed on the first member and an alignment hole defined in the second member, the travel limiter comprising a protrusion extending from the first member towards the second member and an alignment pin defined on the protrusion in alignment with the alignment hole such that when the first and second members are urged towards one another, the protrusion contacts the second member and the alignment pin enters the alignment hole, wherein the travel limiter limits the travel of the first and second members towards one another.

16. A tweezer-like device for holding a dental abutment having a central axis, the device comprising:
  a substantially identical first and second member each having a joined end and a free end, the members being disposed in a V-like configuration with the joined ends interconnected and the free ends spaced apart such that when the members are urged towards one another, the free ends are urged into contact;
  each of the members further having:
    a handle portion including the joined end, the handle portion extending in a first direction,
    a junction segment joined to the handle portion and extending in a second direction which is at an angle to the first direction, and
    a grip segment having a first end joined to the junction segment and a second end configured to grip the dental abutment through cooperative action with the second end of the grip segment of the other member, the grip segment extending in a third direction which is at an angle to the second direction;
  wherein the angle between the first direction and the second direction is in the range of 70 to 110 degrees and the angle between the second direction and the third direction is in the range of 70 to 110 degrees;
  a locking device operable to selectively retain the first and second members in a position such that the free ends are in contact, the locking device comprising a locking arm extending from the first member and having a locking end with a detent defined thereon, the second member having an opening defined therein, the locking arm configured such that the locking end passes through the opening when the members are urged toward one another and the detent engages the opening in the second member to retain the free ends of the members in contact; and
  a travel limiter disposed on the first member and an alignment hole defined in the second member, the travel limiter comprising a protrusion extending from the first member towards the second member and an alignment pin defined on the protrusion in alignment with the alignment hole such that when the first and second members are urged towards one another, the protrusion contacts the second memeber and the alignment pin enters the alignment hole, wherein the travel limiter limits the travel of the first and second members towards one another.

17. The device according to claim 16, wherein the second end of the grip segment retains a dental abutment at an angle in the range of 60 to 90 degrees with respect to the handle portion.

18. The device according to claim 16, wherein the grip segment includes a main portion including the first end and a mid-portion between the main portion and the second end, the mid-portion being angled with respect to the main portion.

19. The device according to claim 18, wherein the angle between the mid-portion and the main portion is in the range of 30 to 50 degrees.

20. The device according to claim 18, wherein the second end is angled with respect to the mid-portion, the angle being in the range of 0 to 30 degrees.

21. A tweezer-like device for holding a dental abutment having a central axis, the device comprising:
  a substantially identical first and second member each having a joined end and a free end, the members being disposed in a V-like configuration with the joined ends interconnected and the free ends spaced apart such that when the members are urged towards one another, the free ends are urged into contact;
  each of the members further having:
    a handle portion including the joined end and having an opposite end; the handle extending in a first direction between the joined and opposite ends,
    a junction segment joined to the opposite end of the handle portion and extending in a second direction, and
    a grip segment having a first end joined to the junction segment and a second end configured to grip the dental abutment through cooperative action with the second end of the grip segment of the other member, the grip segment extending in a third direction;
  wherein a handle plane is defined by the joined ends and opposite ends of the handle, a junction plane is defined by the junction segments, and a grip plane is defined by the grip segments, the junction plane being at an angle of 70 to 110 degrees to the handle plane and the grip plane being at an angle of 70 to 110 degrees to the junction plane; and
  a locking device operable to selectively retain the first and second members in a position such that the free ends are in contact, the locking device comprising a locking arm extending from the first member and having a locking end with a detent defined thereon, the second member having an opening defined therein, the locking arm configured such that the locking end passes through the opening when the members are urged toward one another and the detent engages the opening in the second member to retain the free ends of the members in contact.

22. A tweezer-like device for holding a dental abutment having a central axis, the device comprising:

a substantially identical first and second member each having a joined end and a free end, the members being disposed in a V-like configuration with the joined ends interconnected and the free ends spaced apart such that when the members are urged towards one another, the free ends are urged into contact;

each of the members further having a handle portion including the joined end, and an offset gripping portion;

the gripping portion of each member having a junction segment joined to the handle portion and forming an interior angle in the range of 70 to 110 degrees with the handle portion, the gripping portion further having a grip segment having a first end joined to the junction segment, a main portion including the first end, a second end, and a mid-portion adjacent the second end and disposed between the main portion and the second end, the main portion of the grip segment forming an interior angle in the range of 70 to 110 degrees with the junction segment, the second end of the grip segment configured to grip the dental abutment through cooperative action with the second end of the grip segment of the other member such that the central axis of the dental abutment is retained at an angle in the range of 60 to 90 degrees to the handle portion; and a locking device operable to selectively retain the first and second members in a position such that the free ends are in contact, the locking device comprising a locking arm extending from the first member and selectively engaging the second member.

* * * * *